United States Patent
Huelskamp et al.

(10) Patent No.: US 8,041,431 B2
(45) Date of Patent: Oct. 18, 2011

(54) SYSTEM AND METHOD FOR IN SITU TRIMMING OF OSCILLATORS IN A PAIR OF IMPLANTABLE MEDICAL DEVICES

(75) Inventors: Paul Huelskamp, St. Paul, MN (US); Thomas J. Harris, Shoreview, MN (US); Binh C. Tran, Minneapolis, MN (US); Ramprasad Vijayagopal, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 371 days.

(21) Appl. No.: 12/350,080

(22) Filed: Jan. 7, 2009

(65) Prior Publication Data
US 2009/0177251 A1 Jul. 9, 2009

Related U.S. Application Data

(60) Provisional application No. 61/019,549, filed on Jan. 7, 2008.

(51) Int. Cl.
*A61N 1/00* (2006.01)
(52) U.S. Cl. ........................... 607/60; 607/32
(58) Field of Classification Search .............. 607/32, 607/60; 128/903
See application file for complete search history.

(56) References Cited

U.S. PATENT DOCUMENTS

| | | |
|---|---|---|
| 3,672,352 A | 6/1972 | Summers |
| 4,361,153 A | 11/1982 | Slocum et al. |
| 4,373,527 A | 2/1983 | Fischell |
| 4,481,950 A | 11/1984 | Duggan |
| 4,519,401 A | 5/1985 | Ko et al. |
| 4,573,994 A | 3/1986 | Fischell et al. |
| 4,614,192 A | 9/1986 | Imran et al. |
| 4,616,640 A | 10/1986 | Kaali et al. |
| 4,651,740 A | 3/1987 | Schroeppel |
| 4,793,825 A | 12/1988 | Benjamin et al. |
| 5,113,859 A | 5/1992 | Funke |
| 5,423,334 A | 6/1995 | Jordan |
| 5,778,882 A | 7/1998 | Raymond et al. |
| 5,800,478 A | 9/1998 | Chen et al. |
| 5,814,089 A | 9/1998 | Stokes et al. |
| 5,833,603 A | 11/1998 | Kovacs et al. |
| 6,140,740 A | 10/2000 | Porat et al. |
| 6,141,588 A | 10/2000 | Cox et al. |

(Continued)

FOREIGN PATENT DOCUMENTS

EP 0300552 1/1989

(Continued)

*Primary Examiner* — Niketa Patel
*Assistant Examiner* — Catherine Voorhees
(74) *Attorney, Agent, or Firm* — Faegre & Benson LLP (57) ABSTRACT

A system and method for in situ trimming of oscillators in a pair of implantable medical devices is provided. Each frequency over a range of oscillator trim frequencies for an initiating implantable medical device is selected and a plurality of commands are sent via an acoustic transducer in situ over the frequency selected. Each frequency over a range of oscillator trim frequencies for a responding implantable medical device is selected and a response to each of the commands received is sent via an acoustic transducer in situ over the frequency selected. The responses received by the initiating implantable medical device are evaluated and a combination of the oscillator trim frequencies for both implantable medical devices that together exhibit a strongest acoustic wave is identified. Oscillators in both implantable medical devices are trimmed to the oscillator trim frequencies in the combination identified.

10 Claims, 7 Drawing Sheets

U.S. PATENT DOCUMENTS

| | | | |
|---|---|---|---|
| 6,162,238 A | 12/2000 | Kaplan et al. | |
| 6,164,284 A | 12/2000 | Schulman et al. | |
| 6,170,488 B1 | 1/2001 | Spillman, Jr. et al. | |
| 6,185,452 B1 | 2/2001 | Schulman et al. | |
| 6,200,265 B1 | 3/2001 | Walsh et al. | |
| 6,234,973 B1 | 5/2001 | Meador et al. | |
| 6,236,889 B1 | 5/2001 | Soykan et al. | |
| 6,277,078 B1 | 8/2001 | Porat et al. | |
| 6,308,099 B1 | 10/2001 | Fox et al. | |
| 6,336,903 B1 | 1/2002 | Bardy | |
| 6,368,284 B1 | 4/2002 | Bardy | |
| 6,398,728 B1 | 6/2002 | Bardy | |
| 6,411,840 B1 | 6/2002 | Bardy | |
| 6,431,175 B1 | 8/2002 | Penner et al. | |
| 6,440,066 B1 | 8/2002 | Bardy | |
| 6,442,413 B1 | 8/2002 | Silver | |
| 6,442,433 B1 | 8/2002 | Linberg | |
| 6,445,953 B1 | 9/2002 | Bulkes et al. | |
| 6,453,196 B1 * | 9/2002 | Von Arx et al. | 607/9 |
| 6,456,602 B1 * | 9/2002 | Hwang et al. | 370/307 |
| 6,456,883 B1 | 9/2002 | Torgerson et al. | |
| 6,472,991 B1 | 10/2002 | Schulman et al. | |
| 6,571,128 B2 * | 5/2003 | Lebel et al. | 607/60 |
| 6,628,989 B1 | 9/2003 | Penner et al. | |
| 6,638,231 B2 | 10/2003 | Govari et al. | |
| 6,654,638 B1 | 11/2003 | Sweeney | |
| 6,675,049 B2 | 1/2004 | Thompson et al. | |
| 6,712,772 B2 | 3/2004 | Cohen et al. | |
| 6,764,446 B2 | 7/2004 | Wolinsky et al. | |
| 6,783,499 B2 | 8/2004 | Schwartz | |
| 6,792,311 B2 | 9/2004 | Fox et al. | |
| 6,809,507 B2 | 10/2004 | Morgan et al. | |
| 6,823,031 B1 | 11/2004 | Tatem, Jr. | |
| 6,840,956 B1 | 1/2005 | Wolinsky et al. | |
| 6,855,115 B2 | 2/2005 | Fonseca et al. | |
| 6,895,265 B2 | 5/2005 | Silver | |
| 6,907,285 B2 | 6/2005 | Denker et al. | |
| 6,978,182 B2 | 12/2005 | Mazar et al. | |
| 6,985,773 B2 | 1/2006 | Von Arx et al. | |
| 7,003,350 B2 | 2/2006 | Denker et al. | |
| 7,018,336 B2 | 3/2006 | Enegren et al. | |
| 7,024,248 B2 | 4/2006 | Penner et al. | |
| 7,027,871 B2 | 4/2006 | Burnes et al. | |
| 7,033,322 B2 | 4/2006 | Silver | |
| 7,061,381 B2 | 6/2006 | Forcier et al. | |
| 7,134,999 B2 | 11/2006 | Brauker et al. | |
| 7,187,979 B2 | 3/2007 | Haubrich et al. | |
| 7,198,603 B2 | 4/2007 | Penner et al. | |
| 7,214,189 B2 | 5/2007 | Zdeblick | |
| 7,236,821 B2 | 6/2007 | Cates et al. | |
| 7,273,454 B2 | 9/2007 | Raymond et al. | |
| 7,273,457 B2 | 9/2007 | Penner | |
| 7,399,313 B2 | 7/2008 | Brown et al. | |
| 7,425,200 B2 | 9/2008 | Brockway et al. | |
| 7,452,334 B2 | 11/2008 | Gianchandani et al. | |
| 7,481,771 B2 | 1/2009 | Fonseca et al. | |
| 2001/0043514 A1 | 11/2001 | Kita | |
| 2002/0042561 A1 | 4/2002 | Schulman et al. | |
| 2002/0045812 A1 | 4/2002 | Ben-Haim et al. | |
| 2002/0151770 A1 | 10/2002 | Noll, III et al. | |
| 2002/0183628 A1 | 12/2002 | Reich et al. | |
| 2003/0009204 A1 | 1/2003 | Amundson et al. | |
| 2003/0136417 A1 | 7/2003 | Fonseca et al. | |
| 2003/0181794 A1 | 9/2003 | Rini et al. | |
| 2003/0191383 A1 | 10/2003 | Ben-Haim et al. | |
| 2004/0057340 A1 | 3/2004 | Charles-Erickson et al. | |
| 2004/0064133 A1 | 4/2004 | Miller et al. | |
| 2004/0088009 A1 | 5/2004 | Degroot | |
| 2004/0152999 A1 | 8/2004 | Cohen et al. | |
| 2005/0056539 A1 | 3/2005 | Morgan et al. | |
| 2005/0159789 A1 | 7/2005 | Brockway et al. | |
| 2005/0187482 A1 | 8/2005 | O'Brien et al. | |
| 2005/0215887 A1 | 9/2005 | Ben-Haim et al. | |
| 2005/0242479 A1 | 11/2005 | Petisce et al. | |
| 2006/0004263 A1 | 1/2006 | Feliss et al. | |
| 2006/0009818 A1 | 1/2006 | Von Arx et al. | |
| 2006/0030903 A1 | 2/2006 | Seeberger et al. | |
| 2006/0031378 A1 | 2/2006 | Vallapureddy et al. | |
| 2006/0085039 A1 | 4/2006 | Hastings et al. | |
| 2006/0085041 A1 | 4/2006 | Hastings et al. | |
| 2006/0085042 A1 | 4/2006 | Hastings et al. | |
| 2006/0136004 A1 | 6/2006 | Cowan et al. | |
| 2007/0142728 A1 | 6/2007 | Penner et al. | |
| 2007/0208261 A1 * | 9/2007 | Maniak et al. | 600/509 |
| 2008/0021333 A1 | 1/2008 | Huelskamp | |
| 2008/0021972 A1 | 1/2008 | Huelskamp et al. | |
| 2008/0082146 A1 * | 4/2008 | Gandhi et al. | 607/60 |
| 2008/0114224 A1 * | 5/2008 | Bandy et al. | 600/302 |
| 2008/0129457 A1 | 6/2008 | Ritter et al. | |
| 2008/0288038 A1 * | 11/2008 | Paul et al. | 607/119 |
| 2009/0075687 A1 | 3/2009 | Hino et al. | |
| 2009/0177251 A1 | 7/2009 | Huelskamp et al. | |
| 2009/0198307 A1 | 8/2009 | Mi et al. | |
| 2010/0042177 A1 | 2/2010 | Stahmann et al. | |
| 2010/0198307 A1 | 8/2010 | Toy et al. | |

FOREIGN PATENT DOCUMENTS

| | | |
|---|---|---|
| WO | WO99/34453 | 7/1999 |
| WO | WO99/34731 | 7/1999 |
| WO | WO2004/089465 | 10/2004 |
| WO | WO2006/045073 | 4/2006 |
| WO | WO2006/045074 | 4/2006 |
| WO | WO2006/045075 | 4/2006 |
| WO | WO2006/069215 | 6/2006 |
| WO | 2007070794 | 6/2007 |
| WO | WO2008/011592 | 1/2008 |
| WO | WO2008/011593 | 1/2008 |
| WO | 2009102640 A1 | 8/2009 |

* cited by examiner

SYSTEM AND METHOD FOR IN SITU TRIMMING OF OSCILLATORS IN A PAIR OF IMPLANTABLE MEDICAL DEVICES

CROSS-REFERENCE TO RELATED APPLICATIONS

This non-provisional patent application claims priority under 35 U.S.C. §119(e) to U.S. Provisional Patent application Ser. No. 61/019,549, filed Jan. 7, 2008, the disclosure of which is incorporated by reference.

FIELD

The invention relates in general to oscillator trimming and, specifically, to a system and method for in situ trimming of oscillators in a pair of implantable medical devices.

BACKGROUND

Implantable medical devices (IMDs) can provide in situ physiological data monitoring and therapy delivery, including cardiac defibrillation, pacing and resynchronization, and intracorporeal drug delivery. IMDs function through pre-programmed control over monitoring and therapeutic functions. As required, IMDs can be interfaced to external devices, such as programmers, repeaters, and similar devices, which can program, troubleshoot, and exchange parametric and physiological data through induction or other forms of wireless telemetry.

Implantable sensors monitor and relay physiological data to other devices. Advanced conventional IMDs can be interfaced with implantable sensors directly through wired interconnections, or indirectly via an external intermediary device. Wired interconnections are invasive and require an intrabody tunnel that exposes a patient to adverse side effects, including internal injury, infection, and discomfort. Relay through an external intermediary device requires the periodic upload of stored data, which is only then available to an IMD indirectly by separate download. Thus, the physiological data can go stale before receipt by the IMD.

Alternatively, IMDs can be directly interconnected for data exchange through a wireless intrabody network, such as described in commonly-assigned U.S. Patent Publication No. 2006/0031378, published Feb. 9, 2006, pending, the disclosure of which is incorporated by reference. Multiple IMDs exchange data wirelessly through acoustic or radio frequency (RF) connections. Wireless intrabody interconnection alleviates the need for large onboard storage for holding monitored data, which can instead be immediately exchanged between the multiple IMDs.

Effective wireless intra-IMD communications, though, require maintaining interconnected IMDs in synchrony. Digital components within each device are susceptible to factors affecting performance, such as temperature, age, mechanical and electrical tolerances, and operational environment. Oscillators, for instance, control the timing of IMD operations, but frequency drift, which occurs naturally over time, can skew an oscillator's timing, which in turn skews IMD operation. Similarly, transducers convert electrical signals into and from acoustic energy. Channel characteristics can degrade transducer efficiency. Oscillator frequency drift can further degrade transducer efficiency by skewing transducer operation away from a trim frequency. Conventional IMD synchronization fails to compensate for oscillator-precipitated transducer skew.

U.S. Pat. No. 6,823,031, issued Nov. 23, 2004, to Tatem, Jr., discloses automated frequency compensation for remote synchronization. An oscillator is stepped through offset frequencies that are associated with a lock range of a phase lock loop (PLL). Oscillator frequencies are incremented until a desired result is achieved, after which control reverts back to the PLL. However, the oscillator for a device is trimmed without transducer adjustment.

U.S. Pat. No. 7,187,979, issued Mar. 6, 2007, to Haubrich et al., discloses medical device synchronization with reduced reliance on periodic polling. The internal clocks of two devices, such as an IMD and an external device, can be synchronized by computing time drift as a function of measured skew. In a further embodiment, an IMD is synchronized to a time signal generated by an external time reference with polling performed only when a device is likely to be receptive. However, oscillator synchronization is reliant on an external reference signal and is trimmed without transducer adjustment.

Therefore, an approach is needed to provide intracorporeal trim of transducers of wirelessly interconnected IMDs. Preferably, such an approach would avoid significant depletion of resources.

SUMMARY

The transducers in a pair of IMDs are trimmed through an intracorporeal frequency sweep of their respective oscillators. A search space of oscillator trim frequencies for each IMD is determined. An initiating IMD notifies a responding IMD to begin a sweep of the oscillator trim frequencies. Each IMD selects oscillator trim frequencies through a heuristic mapping of the search space. For each pair of selected oscillator trim frequencies, the initiating IMD repeatedly sends a command and monitors responses received from the responding IMD. The oscillator trim frequency pairing providing the strongest command exchange is selected to trim the transducers. Safe operation is assured by saving the responding IMD's new oscillator trim frequency into volatile memory to permit recovery of the original, albeit possibly non-optimal, oscillator trim frequency if subsequent communication with the initiating IMD fails.

One embodiment provides a system and method for in situ trimming of oscillators in a pair of IMDs. Each frequency over a range of oscillator trim frequencies for an initiating IMD is selected and a plurality of commands are sent via an acoustic transducer in situ over the frequency selected. Each frequency over a range of oscillator trim frequencies for a responding IMD is selected and a response to each of the commands received is sent via an acoustic transducer in situ over the frequency selected. The responses received by the initiating IMD are evaluated and a combination of the oscillator trim frequencies for both IMDs that together exhibit a strongest acoustic wave is identified. Oscillators in both IMDs are trimmed to the oscillator trim frequencies in the combination identified.

A further embodiment provides a system and method for intracorporeal trimming of acoustic transducers for a plurality of interconnected IMDs. A two-dimensional search space is mapped and includes a range of oscillator trim frequencies for an initiating and a responding IMD. On the initiating IMD, a sweep of the oscillator trim frequency ranges is performed that includes selecting each oscillator trim frequency in the search space, and sending a series of commands to the responding IMD at the selected oscillator trim frequency via an acoustic transducer. On the responding IMD, a sweep of the oscillator trim frequency ranges is also performed that includes selecting each oscillator trim frequency in the search space, and sending a response to each command that is received to the initiating IMD at the selected oscillator trim frequency via an acoustic transducer. The responses received by the initiating IMD from the responding IMD evaluated and the oscillator trim frequencies indicating a strongest acoustic wave are selected. The oscillators on both IMDs are set to the selected oscillator trim frequencies.

Still other embodiments will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Figure 1:
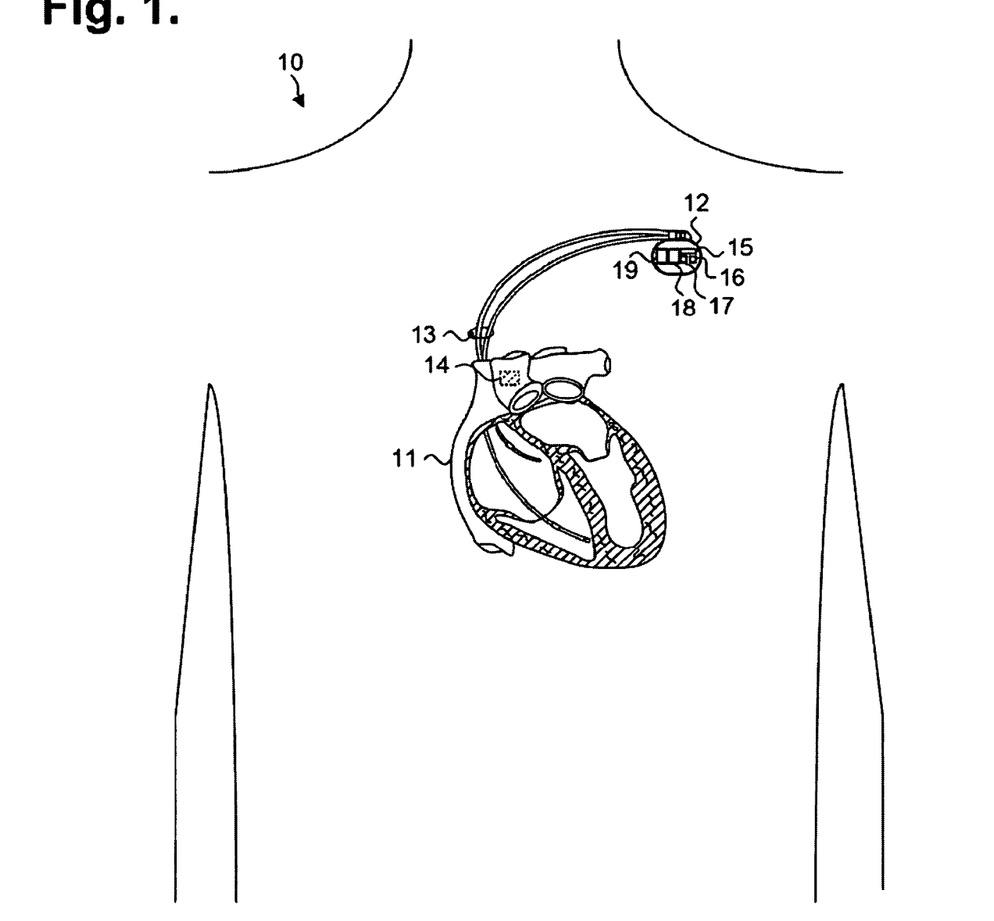
FIG. 1 is a block diagram showing a system for in situ trimming of oscillators in a pair of implantable medical devices, in accordance with one embodiment.

Although described in relation to medical devices intended for providing cardio and cardiopulmonary diagnosis, therapy, or monitoring, the embodiments described apply generally to all implantable medical devices and sensors capable of wireless intracorporeal interconnection and remotely interrogated or programmed.
System Recent advances in microelectronics have made direct IMD-to-IMD, including IMD-with-implantable sensor, intercommunications via wireless acoustic telemetry commercially practicable. FIG. 1 is a block diagram showing a system 10 for in situ trimming of oscillators in a pair of IMDs 12, 14, in accordance with one embodiment. The IMDs 12, 14 together form a wireless intrabody network, which facilitates direct intracorporeal IMD-to-IMD data exchange, such as described in commonly-assigned U.S. Patent Publication No. 2006/0031378, published Feb. 9, 2006, pending, the disclosure of which is incorporated by reference.

By way of example, a therapeutic IMD 12, such as a cardiac therapy device, is paired with a monitoring IMD 14, such as a cardiac monitoring device. Cardiac therapy devices include pacemakers, implantable cardioverter-defibrillators, biventricular pacemakers, and similar devices. The therapeutic IMD 12 is surgically implanted in the chest, abdomen, or other internal bodily location of a patient 10 and includes physically attached components, such as leads 13 for providing monitoring within and for delivering therapy to the patient's heart 11. The monitoring IMD 14 is deployed intravascularly through a catheter into the left coronary artery or other internal bodily location, or implanted in similar fashion as the therapeutic IMD 12. The monitoring IMD 14 is self-contained and may not be intended for surgical access or removal. Other forms of IMD and components are possible.

Figure 12:
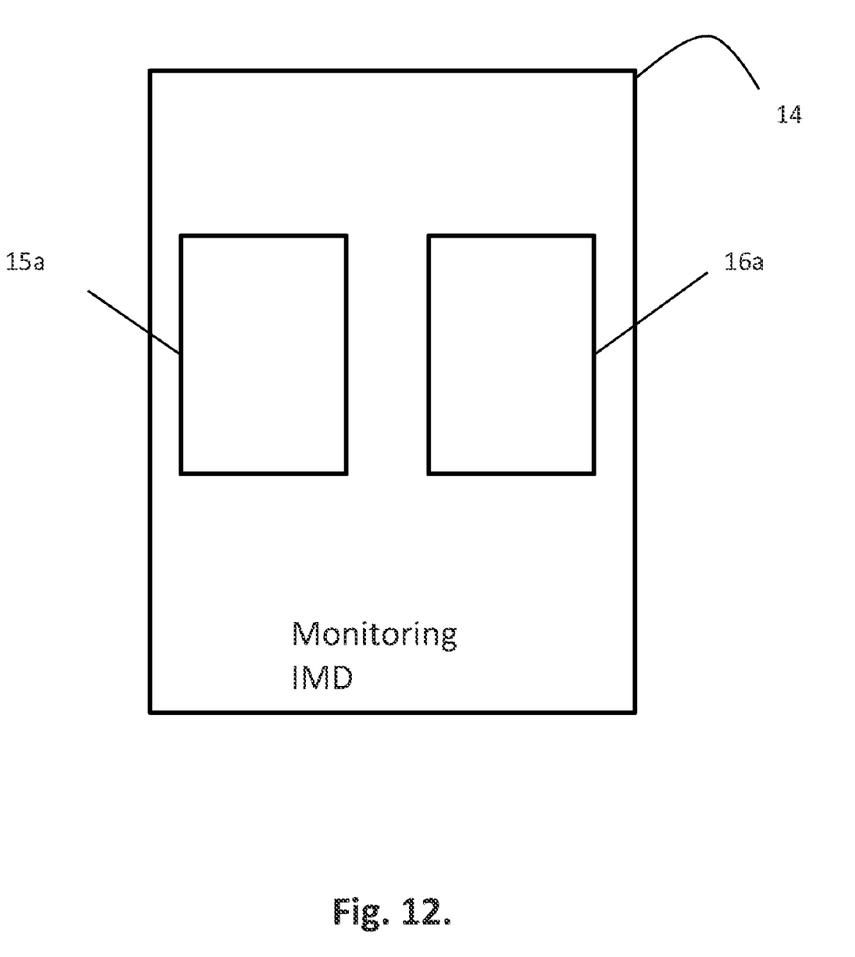
FIG. 12 is a block diagram showing several illustrative operational components of the monitoring implantable medical device of FIG. 1.

Each IMD 12, 14 encloses operational circuitry within a hermetically-sealed housing. Referring to the therapeutic IMD 12, the operational circuitry generally includes a transducer 15; oscillator 16; control circuitry 17; memory 18; and power source 19, which provides a finite power supply for the operational circuitry. The monitoring IMD 14 also includes operational circuitry such as a transducer 15a and oscillator 16a, as further shown, for example, in FIG. 12. The transducer 15 provides signal conversion, including converting internal electrical signals into and from acoustic energy for intracorporeal data exchange with other IMDs, such as the monitoring IMD 14. Periodically, or as needed, the IMDs' transducers are synchronized and trimmed through an intracorporeal frequency sweep, as further described below beginning with reference to FIG. 4. The oscillator 16 regulates internal device operation by controlling and synchronizing the timing of IMD operations. The control circuitry 17 implements the device's functionality, such as therapy delivery or physiometric monitoring, and enables testing, selection, synchronization, and storage of oscillator trim frequencies. Finally, the memory 18 stores recorded data, such as the monitored physiometry of the patient 10; environmental data, for instance, ambient body temperature or time of day; and parametric settings, including programming, device status, and operational characteristics. The memory 18 can include both volatile memory, such as DRAM, and non-volatile memory. such as EEPROM. A reference oscillator trim frequency for the oscillator 16 is maintained in the non-volatile memory. Therapeutic and monitoring IMDs have operational circuitry that also includes an external telemetry interface (not shown) for RF, acoustic, or other forms of wireless data exchange with external devices, such as programmers, repeaters, and similar devices. The monitoring IMDs similarly have telemetry circuitry to communicate with external devices directly when interrogated. Other components can be used and data is possible.

In a further embodiment, the patient data can be evaluated, either by an IMD 12, 14, or an external device, for the occurrence of one or more chronic or acute health conditions, such as described in related, commonly-owned U.S. Pat. No. 6,336,903, to Bardy, issued Jan. 8, 2002; U.S. Pat. No. 6,368, 284, to Bardy, issued Apr. 9, 2002; U.S. Pat. No. 6,398,728, to Bardy, issued Jun. 4, 2002; U.S. Pat. No. 6,411,840, to Bardy, issued Jun. 25, 2002; and U.S. Pat. No. 6,440,066, to Bardy, issued Aug. 27, 2002, the disclosures of which are incorporated by reference.

In a still further embodiment, the patient data is extracorporeally safeguarded against unauthorized disclosure to third parties, including during collection, assembly, evaluation, transmission, and storage, to protect patient privacy and comply with recently enacted medical information privacy laws, such as the Health Insurance Portability and Accountability Act (HIPAA) and the European Privacy Directive. At a minimum, patient health information that identifies a particular individual with health- and medical-related information is treated as protectable, although other types of sensitive information in addition to or in lieu of specific patient health information could also be protectable.

Oscillator and Transducer Frequency Trim

Figure 2:
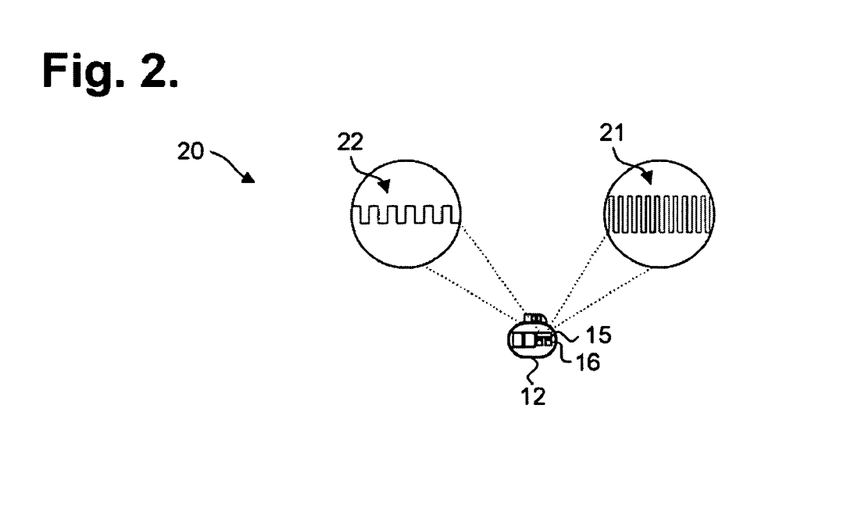
FIG. 2 is a timing diagram showing, by way of example, oscillator and transducer trim frequencies.

In general, an oscillator regulates the timing of operations performed by digital components within an IMD, which has a direct affect on the operation of a transducer. FIG. 2 is a timing diagram 20 showing, by way of example, oscillator and transducer trim frequencies. The oscillator 16 operates at a frequency 22 determined through oscillation of a clock crystal, such as a quartz crystal. For example, an oscillator with a desired frequency operating point of 40 kHz might be specified with an operating frequency range of 37 kHz to 43 kHz. The transducer 15 converts internal electrical signals into and from acoustic energy at the oscillator's frequency 22. Over time, however, the center trim frequency 21 of the transducer 15 may drift and lose synchrony with the oscillator's frequency 22.

Figure 3:
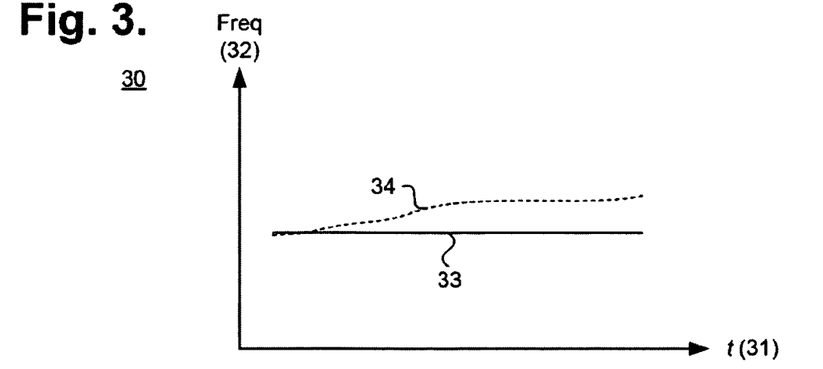
FIG. 3 is a graph showing, by way of example, oscillator drift.

As required, to restore transducer efficiency and synchrony, the oscillator 16 must be trimmed. FIG. 3 is a graph 30 showing, by way of example, oscillator drift. The x-axis 31 represents time t and the y-axis 32 represents frequency in kilohertz (kHz). Ideally, an oscillator 16 will consistently maintain a fixed trimmed frequency 33 indefinitely. However, in practice, the trimmed frequency 34 may drift over time to a faster rate (as depicted) or slower rate, generally over the course of several years.

Figure 4:
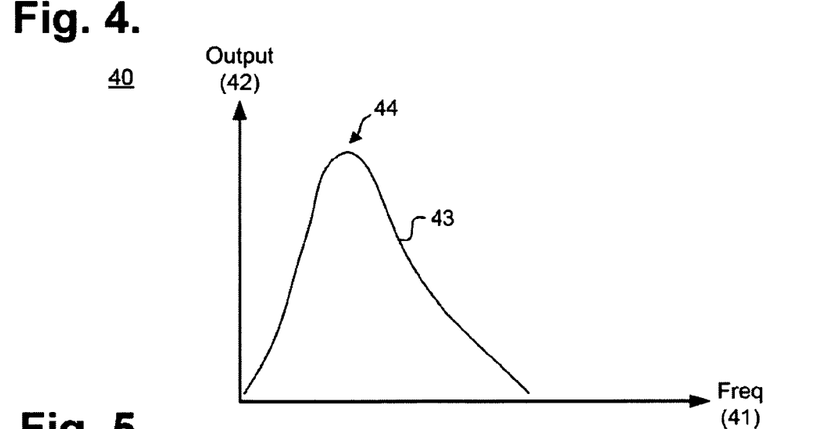
FIG. 4 is a graph showing, by way of example, transducer frequency response.

The transducer 15 has a response based on the frequency of the exciting signal. FIG. 4 is a graph 40 showing, by way of example, transducer frequency response. The x-axis 41 represents frequency in kilohertz (kHz) and the y-axis 42 represents peak transducer output in Pascals. The transducer's output response 43 can be expressed as a function of frequency. Typically, a transducer 15 will have a "center" frequency 44, which is the frequency at which the transducer 15 outputs a peak signal. The oscillator 16 is trimmed to the center frequency 44 of the transducer 15 to achieve maximum signal strength.

Figure 5:
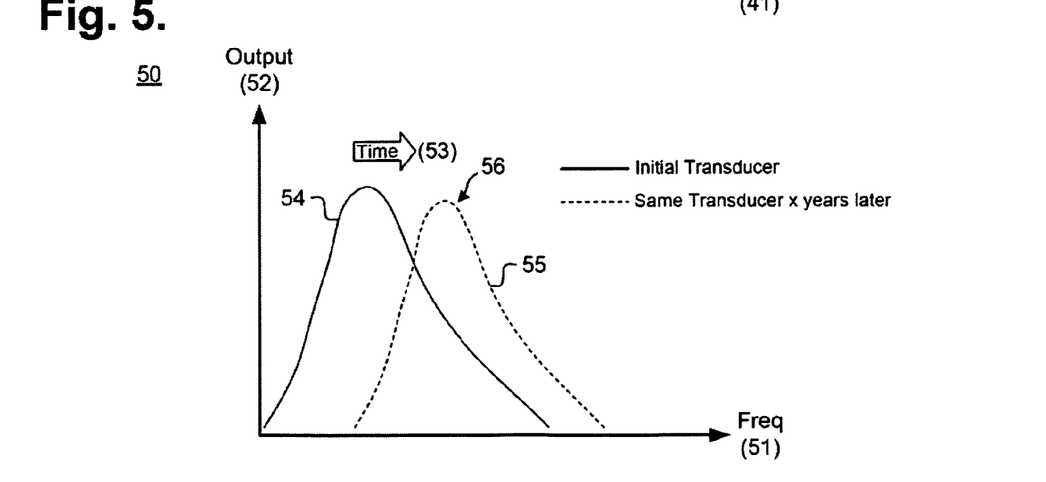
FIG. 5 is a graph showing, by way of example, transducer frequency response drift.

Over time, the transducer's output response curve can change. FIG. 5 is a graph 50 showing, by way of example, transducer frequency response drift. The x-axis 51 represents frequency in kilohertz (kHz) and the y-axis 52 represents peak transducer output in Pascals. The transducer's initial output response 54 may change over time 53 to a new, shifted output response 55 that causes the center frequency 56 to drift to a faster or slower rate. The resulting skew in center frequency 56 can result in reduced transducer performance or, when severe, degradation or complete disablement of communications. The skew can be the result of various factors, including the aging of components, temperature, electromechanical tolerances, and operational environs. To correct transducer operation, the oscillator 16 must be trimmed to compensate for the skew and restore operation at the transducer's new center frequency 56.

Method

Figure 6:
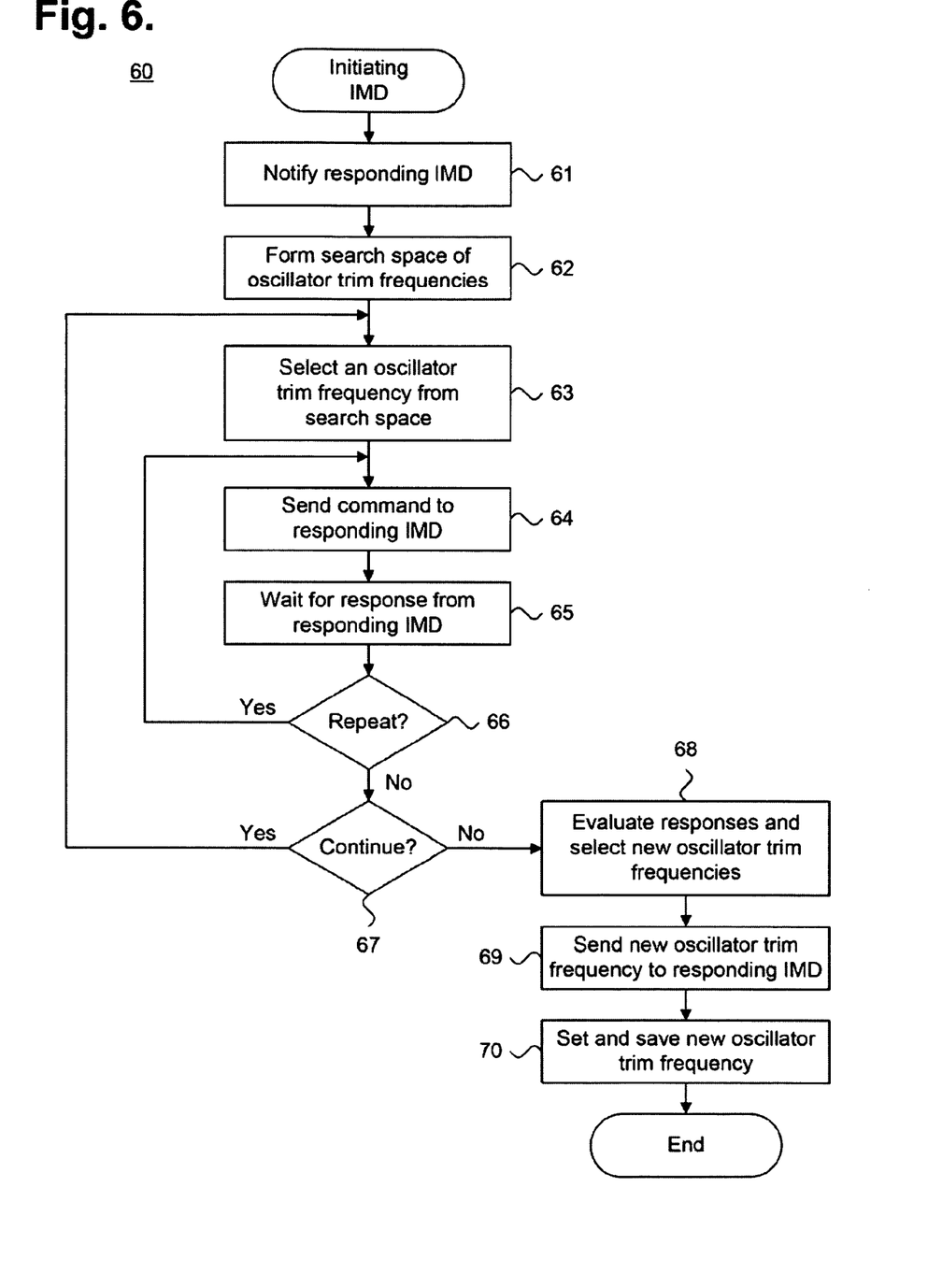
FIGS. 6 and 7 are flow diagrams showing a method for in situ trimming of oscillators in a pair of implantable medical devices, in accordance with one embodiment.
Figure 7:
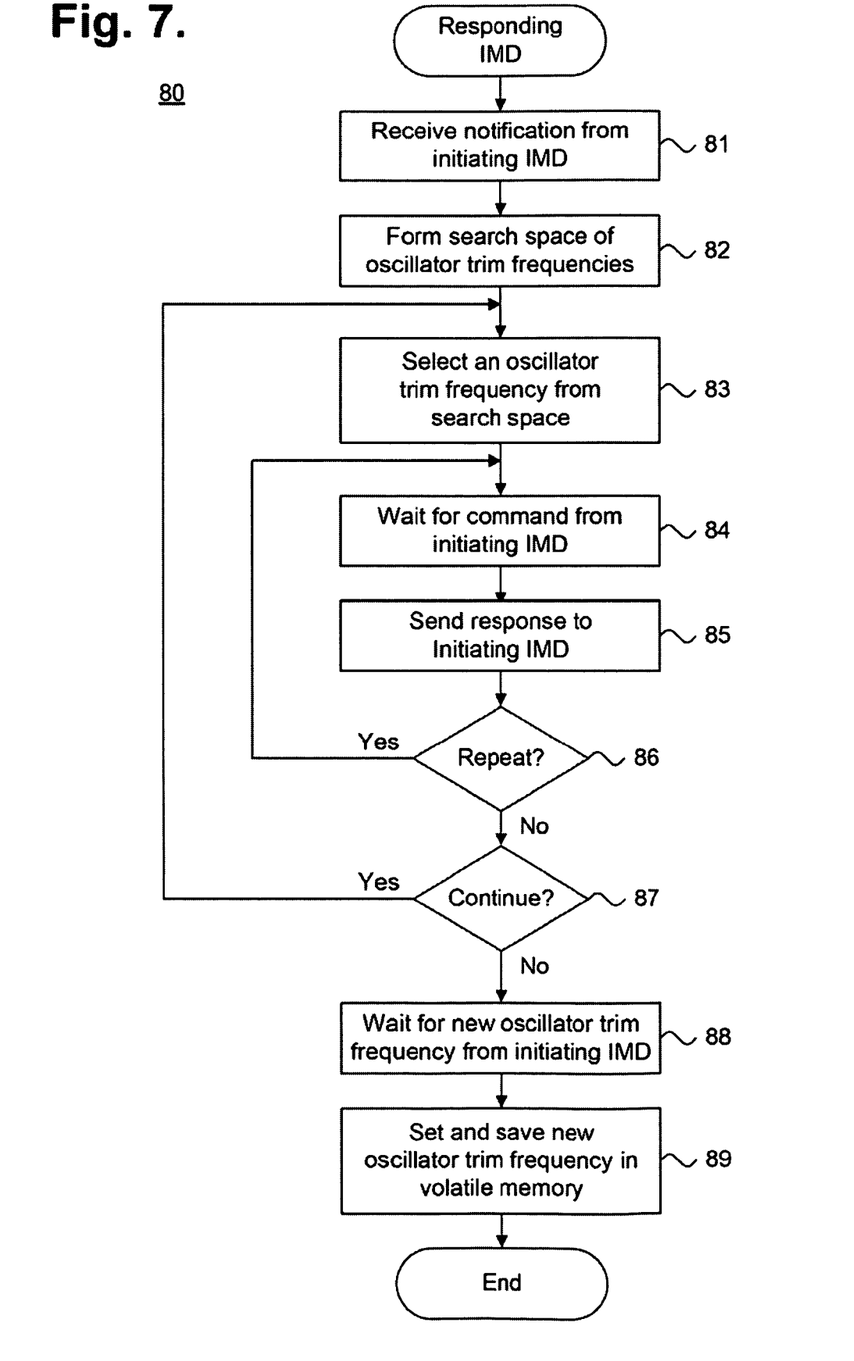

The transducers for a pair of IMDs can be safely and efficiently trimmed by performing a sweep through their respective oscillator trim frequency ranges. The trim frequency ranges can be mapped heuristically. FIGS. 6 and 7 are flow diagrams 60, 80 showing a method for in situ trimming of oscillators in a pair of implantable medical devices, in accordance with one embodiment. The method has two parts, which are respectively performed by an initiating IMD that starts a oscillator frequency sweep, and a responding IMD that receives a new oscillator frequency upon completion of the sweep.

Referring first to FIG. 6, an initiating IMD orchestrates each sweep. As preparatory steps, the initiating IMD notifies a responding IMD to prepare for a sweep (step 61) and forms a search space of oscillator trim frequencies (step 62), such as further described below with reference to FIGS. 8-10. Thereafter, the initiating IMD steps or iterates through the search space (steps 63-67). During each iteration, the initiating IMD first selects an oscillator trim frequency from the search space (step 63) and repeatedly sends a series of commands to the responding IMD (steps 64-66). Each successive oscillator trim frequency is selected using a fixed frequency step size, such as 300 Hz. For each command series, the initiating IMD sends a command to the responding IMD at the currently selected oscillator trim frequency (step 64) and waits for a response from the responding IMD (step 65). The command series (steps 64-66) is preferably repeated (step 66) for a predetermined number of iterations. Repeating the sending of the command series facilitates finding the strongest oscillator trim frequency for exchange with the responding IMD. Similarly, the iteration (steps 63-67) continues (step 67) until the sweep has completed. Completion depends upon the form of heuristic mapping used to move through the search space.

Upon completion of the sweep, the initiating IMD evaluates the responses received from the responding IMD during each iteration and selects a new combination of oscillator trim frequencies for both of the IMDs (step 68). The new oscillator trim frequencies are selected based on the strongest acoustic wave observed, which could be indirectly indicated by the number of responses that the initiating IMD successfully received back from the responding IMD by directly reading the signal-to-noise ratio, or by making other quantitative measurement of signal strength. For instance, a suboptimal oscillator trim frequency pairing might result in only a few of the commands being successfully received by the responding IMD, or in a low signal-to-noise ratio. The responding IMD would respond to the received commands, yet the suboptimal frequency pairing might also result in even fewer responses being successfully received by the initiating IMD. A frequency pairing exhibiting higher rates of command and response receipts would indicate a stronger acoustic wave, or a high signal-to-noise ratio. Other oscillator trim frequency selection criteria are possible. The new oscillator trim frequency is sent to the responding IMD (step 69). Similarly, the new oscillator trim frequency for the initiating IMD is set and saved (step 70), after which transducer trimming is complete.

Figure 8:
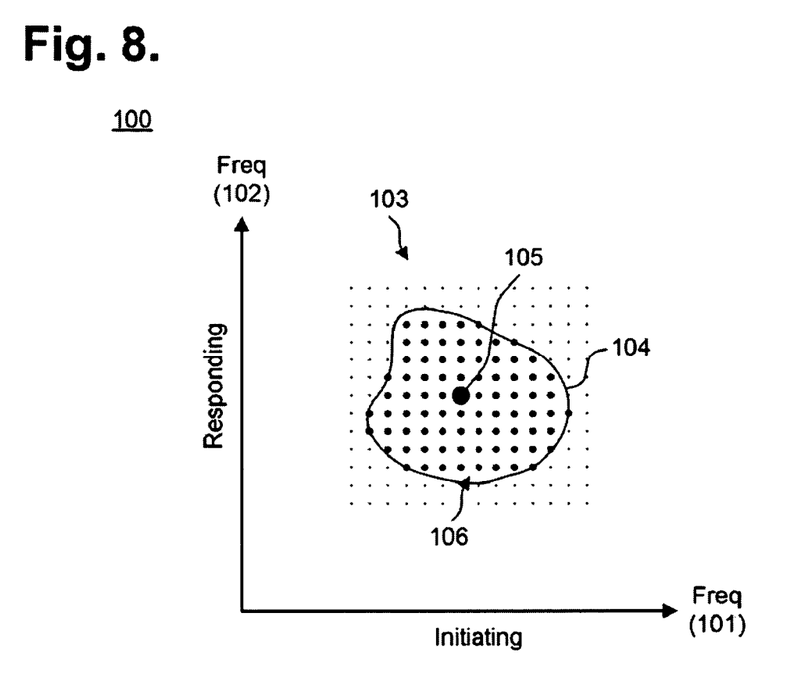
FIGS. 8-10 are topologic diagrams showing, by way of example, oscillator trim frequency search space mappings.
Figure 9:
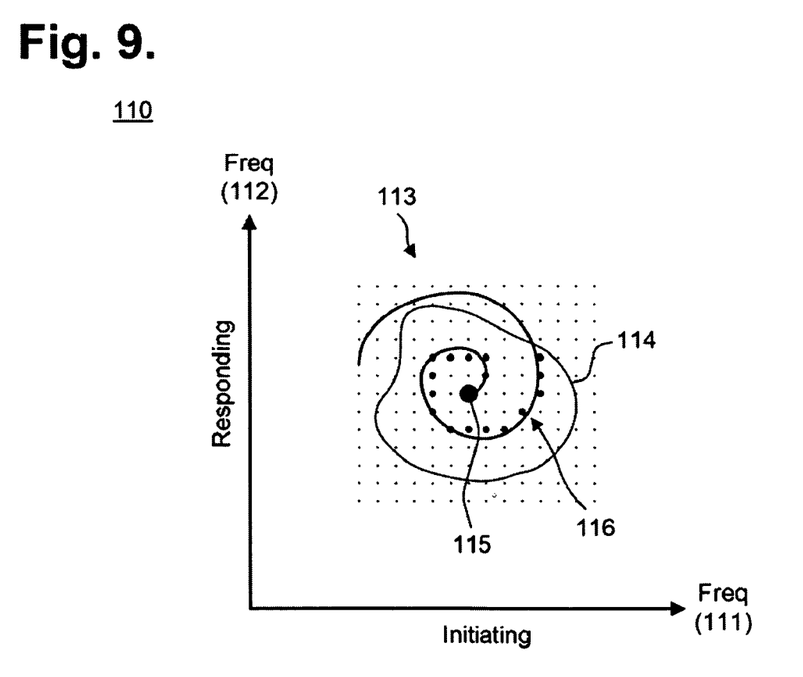
Figure 10:
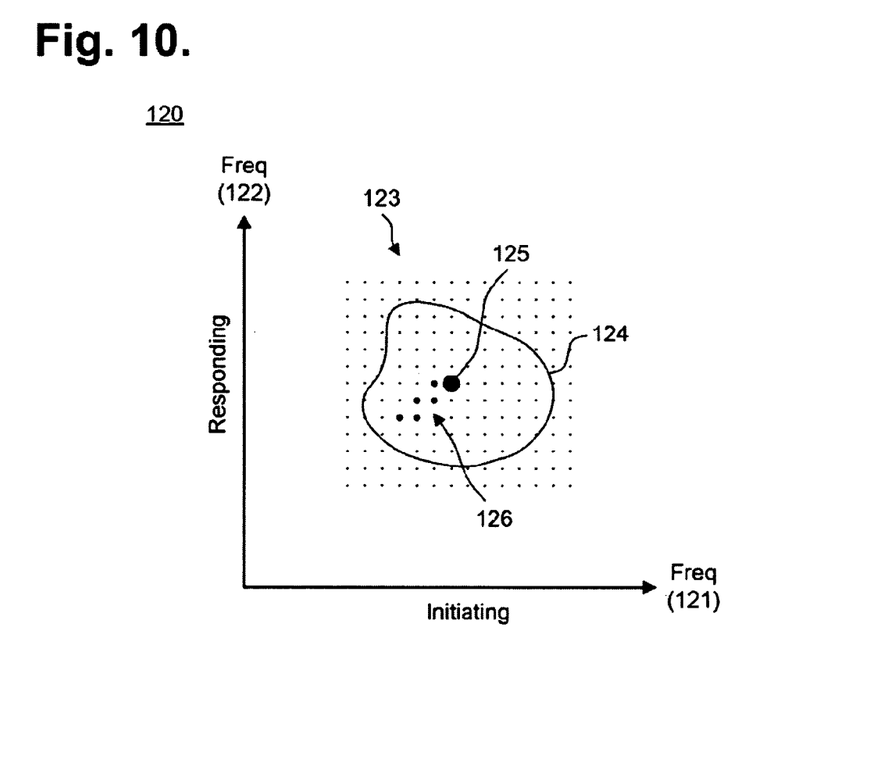

Referring next to FIG. 7, a responding IMD reacts to receipt of a notification to prepare for a sweep from an initiating IMD (step 81) by also forming a search space of oscillator trim frequencies (step 82), as further described below with reference to FIGS. 8-10. Thereafter, the responding IMD steps or iterates through the search space (steps 83-87) in a manner similar to the initiating IMD. During each iteration, the responding IMD first selects an oscillator trim frequency from the search space (step 83) and repeatedly responds to the initiating IMD (steps 84-86). Repeated responses allows the initiating IMD to count and compose the number of responses sent by the responding IMD for each commands sent. During each response, the responding IMD waits for a command from the initiating IMD at a selected oscillator trim frequency (step 84) and then sends a response in reply (step 85). The responses (steps 84-86) are repeated (step 86) for a predetermined number of iterations. Similarly, the iteration (steps 83-87) continues (step 87) until the sweep has completed, which will depend upon the heuristic mapping used to move through the search space.

Upon completion of the sweep, the responding IMD waits to receive a new oscillator trim frequency from the initiating IMD (step 88). Upon receipt, the new oscillator trim frequency for the responding IMD is set and saved into volatile memory (step 89), after which transducer trimming is complete.

As the new oscillator trim frequency is stored in volatile memory, the new frequency is only temporarily retained. A reference oscillator trim frequency for the oscillator 16 is permanently maintained in the non-volatile memory. Thus, should the new oscillator trim frequency prove too aggressive or ineffective, thereby resulting in loss of communications or device error, the reference oscillator trim frequency can be automatically recovered from the non-volatile memory. The volatile memory is cleared, generally by performing a device reset or by allowing the responding IMD to enter a standby or sleep mode, which causes the new oscillator trim frequency to be erased. Following erasure of the volatile memory, the responding IMD reverts back to the reference oscillator trim frequency maintained in the non-volatile memory and resumes normal operation.

In a further embodiment, the new oscillator trim frequency can later be stored into non-volatile memory upon receiving a command to permanently store the frequency. The initiating IMD will generally issue the command to the responding IMD only after first confirming that the new oscillator trim frequency is reliable and safe and can be used without adverse effect to device operation.

Oscillator Trim Frequency Search Space Mappings

Both initiating and responding IMDs perform a sweep of possible oscillator trim frequencies to determine the best frequency pairing. The complete search space can be expressed as an n×m matrix, where there are n possible initiating IMD oscillator frequencies and there are m possible responding IMD oscillator frequencies. FIGS. 8-10 are topologic diagrams 100, 110, 120 showing, by way of example, oscillator trim frequency search space mappings. The x-axes 101, 111, 121 represent initiating IMD oscillator frequencies and the y-axes 102, 112, 122 represent the responding IMD oscillator frequencies. Complete oscillator trim frequency search spaces 103, 113, 123 are depicted. However, for efficiency, the oscillator trim frequency sweeps are limited to only those frequencies that provide acceptable levels of transducer signal strength, as appearing within the enclosed areas 104, 114, 124 of each search space. The enclosed areas 104, 114, 124 can be defined through frequency ranges, such as 37 kHz to 43 kHz. Acceptable transducer signal strengths can be determined prior to implant by bench or empirical testing, or in situ, such as by evaluating observed acoustic waves post-trimming and applying a minimum response cutoff criteria.

Each sweep through the oscillator trim frequency search spaces simultaneously exercises the oscillators and transducers of both IMDs to enable identification of a locally optimal pairing of oscillator trim frequencies. Referring first to FIG. 8, an exhaustive sweep 106 of the entire frequency search space 103 can be performed. During each step or iteration of the sweep, the initiating and responding IMDs each select one of their respective oscillator frequencies from the bounded set of acceptable frequency pairings 104 and a command series is performed. The sweep 104 continues until all frequency pairings within the bounded set of acceptable frequency pairings 124 have been tested, or testing is otherwise terminated. In a further embodiment, the sweep can start from an initial reference oscillator frequency pairing 105, such as a default pre-selected pairing or a frequency pairing picked at time of manufacture or implant.

An exhaustive sweep 106 tests the entire search space, but at the expense of onboard resource depletion and time. The sweep can be made more efficient by testing only a representative subset of the search space. Referring next to FIG. 9, a search through select oscillator trim frequency pairings 116 can be performed, in accordance with a further embodiment. Pairings can be efficiently identified within a subset of the search space 114 by first having the initiating IMD perform a frequency sweep with the responding IMD set to a fixed frequency. The initiating IMD then locks on to its own optimum frequency and asks the responding IMD to perform a frequency sweep. At each step, the frequency sweep can be performed in steps of fixed frequency size, such as ±500 Hz. The end result of the frequency change strives to arrive at a better bit error rate than the previous step. The process is repeated several times, thus following the most efficient path within the search space to get to the optimum frequency pairing 116 within the search space. The process stops when successive frequency changes do not yield a bit error rate that is significantly better than the previous steps, or testing is otherwise terminated.

Various selection criteria may apply in deciding the representative subset of the search space. For example, a search path can be mapped from an initial reference oscillator frequency pairing 115 by mapping a spiral search pattern through the search space. A spiral search pattern can be expressed in polar coordinates by selecting those oscillator frequency pairings located at a radius r specified as a continuous monotonic function of an angle $\theta$, which is initially measured from the reference oscillator frequency pairing 115. Those oscillator frequency pairings falling within a fixed distance of the search path are selected and evaluated, thereby requiring fewer pairings to exercise the oscillators and transducers of the initiating and responding IMDs. Other search path shapes and patterns are possible.

The selective sweep 116 tests a representative part or subset of the search space, yet does not take into consideration whether the search path is producing hopeful or unpromising results. The sweep can be further improved by progressively evaluating interim oscillator trim frequency pairings. Referring to FIG. 10, a progressive search through the bounded set of acceptable frequency pairings 124 can be performed to eliminate those paths within the search space that likely would result in inoperative or less efficient results, in accordance with a still further embodiment. Beginning with an initial reference frequency oscillator frequency pairing 125, immediately adjacent frequency pairings are selected in breadth-first fashion. Only those frequency pairings 126 that reflect improved signal strength remain as possible candidates for the next iterative sweep. The improvement in signal strength can be quantified as a fixed or relative improvement in number of commend responses received or higher signal-to-noise ratio. Other quantitative measures could be applied, such as signal-to-noise ratio, energy received, corrected bits, or bit error rate. The sweep 124 continues until the no further improvements in performance are found, the edge of the bounded set of acceptable frequency pairings 124 is encountered, or testing is otherwise terminated. Other forms of progressive searching are possible.

Oscillator Synchronization

In a further embodiment, the oscillators of the initiating and responding IMDs can be synchronized. During trimming of the transducers, oscillator frequencies may be increased or decreased based on transducer response. Actual oscillator frequencies are not measured and may be unknown due to drift.

Figure 11:
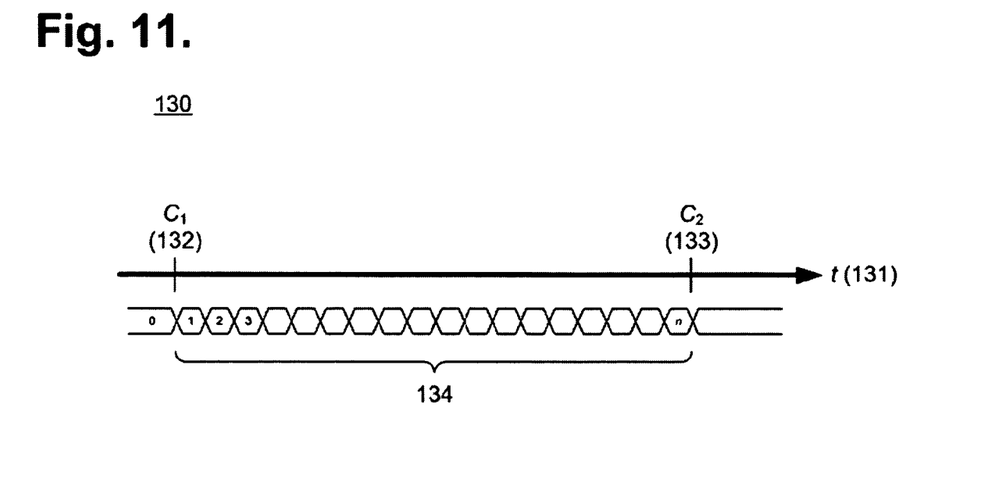
FIG. 11 is a timing diagram showing, by way of example, intracorporeal synchronization of oscillators in interconnected IMDs, in accordance with a further embodiment.

A short command sequence can be used to synchronize the oscillators. FIG. 11 is a timing diagram 130 showing, by way of example, intracorporeal synchronization of oscillators in interconnected IMDs, in accordance with a further embodiment. The x-axis 131 represents time t. The initiating IMD sends a short command sequence to identify frequency skew in the responding IMD's oscillator. The initiating IMD relies on a quartz-controlled reference oscillator frequency against which the responding IMD's oscillator is timed. The responding IMD starts a clock pulse counter (operation 132) upon receipt of a first command $C_1$ from the initiating IMD. The responding IMD continues to count clock pulses until receipt 133 of a second command $C_2$ from the initiating IMD. The clock pulse count 134 is provided to the initiating IMD, which can compare the measured clock pulse count 134 to an expected clock pulse count and establish the responding IMD's actual oscillator frequency. The oscillator frequency can then be provided to the responding IMD for synchronization. Other forms of oscillator synchronization are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A system for in situ trimming of oscillators in a pair of implantable medical devices, comprising:
    an initiating implantable medical device, comprising:
        an oscillator configured for regulating the timing of one or more operations performed by the initiating implantable medical device;
        control circuitry configured to select at least one first oscillator frequency over a range of oscillator trim frequencies; and
        an acoustic transducer configured to send a command in situ over each oscillator frequency selected over the range of oscillator trim frequencies;
    a responding implantable medical device, comprising:
        an oscillator configured for regulating the timing of one or more operations performed by the responding implantable medical device;
        control circuitry configured to select at least one second oscillator frequency over the range of oscillator trim frequencies; and
        an acoustic transducer configured to send a response to each of the commands received in situ over each oscillator frequency selected by each implantable medical device;
    wherein the acoustic transducer of the initiating implantable medical device is configured to receive the responses from the responding implantable medical device; and
    wherein the control circuitry of the initiating implantable medical device is further configured to evaluate the responses received by the initiating implantable medical device to identify a combination of oscillator trim frequencies from the at least one first oscillator frequency of the initiating implantable medical device and the at least one second oscillator frequency of the responding implantable medical device that together exhibit a strongest acoustic wave; and wherein both implantable medical devices are configured to trim the oscillators to the identified combination of oscillator trim frequencies.

2. A system according to claim 1, further comprising:
    on the responding implantable medical device, non-volatile memory in which a reference oscillator trim frequency is maintained and volatile memory in which an identified oscillator trim frequency is stored,
    wherein the control circuitry of the responding implantable medical device is further configured to automatically recover the reference oscillator trim frequency through erasure of the volatile memory.

3. A system according to claim 2, wherein the control circuitry of the responding implantable medical device is further configured to replace the reference oscillator trim frequency maintained in the non-volatile memory with the identified oscillator trim frequency stored in the volatile memory.

4. A system according to claim 1, wherein the acoustic transducer of the initiating implantable medical device is further configured to send a start command and an end command in situ, and the control circuitry of the responding implantable medical device is further configured to commence a clock pulse count upon receipt of the start command, to stop the clock pulse count upon receipt of the end command, and to provide the clock pulse count to the initiating implantable medical device via the acoustic transducer in situ, and further comprising:
    evaluation circuitry configured to establish an actual oscillator frequency in use by the responding implantable medical device by evaluating the clock pulse count, and to provide the actual oscillatory frequency to the responding implantable medical device.

5. A system according to claim 1, further comprising:
    a memory configured to logically map the ranges of the oscillator trim frequencies for both implantable medical devices into a search space, wherein the oscillator frequencies selected are picked by both of the implantable medical devices by heuristically sweeping over the search space in a search pattern comprising one of an exhaustive, a selective, and a progressively-defined grid.

6. A method for in situ trimming of oscillators in a pair of implantable medical devices, comprising:
    selecting at least one first oscillator frequency over a range of oscillator trim frequencies for an initiating implantable medical device and sending a command via an acoustic transducer in situ over each oscillator frequency selected over the range of oscillator trim frequencies;
    selecting at least one second oscillator frequency over the range of oscillator trim frequencies for a responding implantable medical device and sending a response to each of the commands received via an acoustic transducer in situ over each oscillator frequency selected by each implantable medical device;
    evaluating each response received by the initiating implantable medical device and identifying a combination of oscillator trim frequencies from the at least one first oscillator frequency of the initiating implantable medical device and the at least one second oscillator frequency of the responding implantable medical device that together exhibit a strongest acoustic wave; and
    trimming oscillators in both implantable medical devices to the identified combination of oscillator trim frequencies.

7. A method according to claim 6, further comprising:
    on the responding implantable medical device, maintaining a reference oscillator trim frequency in non-volatile memory and storing at least one identified oscillator trim frequency in volatile memory; and
    automatically recovering the reference oscillator trim frequency for the responding implantable medical device through erasure of the volatile memory.

8. A method according to claim 7, further comprising:
    replacing the reference oscillator frequency maintained in the non-volatile memory with the at least one identified oscillator trim frequency stored in the volatile memory.

9. A method according to claim 6, further comprising:

sending a start command from the initiating implantable medical device via the acoustic transducer in situ;

commencing a clock pulse count on the responding implantable medical device upon receipt of the start command;

sending an end command from the initiating implantable medical device via the acoustic transducer in situ;

stopping the clock pulse count on the responding implantable medical device upon receipt of the end command and providing the clock pulse count to the initiating implantable medical device via the acoustic transducer in situ;

establishing an actual oscillator frequency in use by the responding implantable medical device by evaluating the clock pulse count; and providing the actual oscillatory frequency to the responding implantable medical device.

10. A method according to claim 6, further comprising:

logically mapping the ranges of the oscillator trim frequencies for both the initiating and responding implantable medical devices into a search space;

picking the oscillator frequencies selected by heuristically sweeping over the search space in a search pattern comprising one of an exhaustive, a selective, and a progressively-defined grid.

* * * * *